United States Patent
Tchon et al.

(10) Patent No.: US 10,596,281 B1
(45) Date of Patent: Mar. 24, 2020

(54) STERILIZING TOUCH SCREEN DISPLAYS WITH ULTRAVIOLET LIGHT

(71) Applicant: Rockwell Collins, Inc., Cedar Rapids, IA (US)

(72) Inventors: Joseph L. Tchon, Cedar Rapids, IA (US); Brian W. Walker, Cedar Rapids, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 0 days.

(21) Appl. No.: 16/042,245

(22) Filed: Jul. 23, 2018

(51) Int. Cl.
  *A61N 2/10* (2006.01)
  *A61L 2/10* (2006.01)
  *H05B 33/08* (2020.01)
  *A61L 2/24* (2006.01)
  *G06F 3/041* (2006.01)

(52) U.S. Cl.
  CPC .............. *A61L 2/10* (2013.01); *A61L 2/24* (2013.01); *G06F 3/0412* (2013.01); *H05B 33/0842* (2013.01)

(58) Field of Classification Search
  CPC ..... A61L 2/08; A61L 2/10; A61L 2/24; G06F 3/0412; H05B 33/0842
  See application file for complete search history.

(56) References Cited

U.S. PATENT DOCUMENTS

| | | | |
|---|---|---|---|
| 10,139,957 B2 * | 11/2018 | Cohen | A61L 2/10 |
| 2010/0171946 A1 * | 7/2010 | Hecker | G02B 21/084 |
| | | | 356/128 |
| 2011/0256019 A1 * | 10/2011 | Gruen | A61L 2/10 |
| | | | 422/24 |
| 2013/0045132 A1 * | 2/2013 | Tumanov | A61L 2/10 |
| | | | 422/24 |
| 2016/0303394 A1 * | 10/2016 | Hayashi | A61N 5/0614 |
| 2017/0228095 A1 * | 8/2017 | Domaradzki | G06F 3/014 |
| 2017/0333582 A1 * | 11/2017 | Davis | A61L 2/10 |

* cited by examiner

*Primary Examiner* — David E Smith
(74) *Attorney, Agent, or Firm* — Suiter Swantz pc llo

(57) ABSTRACT

A touch screen or touch screen appliance includes built-in UV LEDs. The LEDs sterilize the touch screen at start-up, and periodically during operation. The LEDs may be disposed at the edges of the glass display such that the UV light is completely internally reflected within the glass display to prevent damage or strain to the user's eyes. Alternatively, the LEDs may be disposed behind the glass display, potentially also behind a UV fluorescing or phosphorescing layer to sterilize the glass from behind. Alternatively, the LEDs may be disposed in a layer in front of the glass display, or at angles around the perimeter of the glass display.

18 Claims, 5 Drawing Sheets

US 10,596,281 B1

STERILIZING TOUCH SCREEN DISPLAYS WITH ULTRAVIOLET LIGHT

BACKGROUND

Touch screens in a multi-user environment represent a significant risk of spreading germs. Especially in aircraft, different pilots may operate the same aircraft in a short span of time and pilots debilitated by sickness could be economically harmful. Manual cleaning is inconsistent and unreliable. Therefore, there is a need for a device and method to sterilize touch screens.

SUMMARY

In one aspect, embodiments of the inventive concepts disclosed herein are directed to a touch screen with built-in ultraviolet (UV) light-emitting diodes (LEDs). The LEDs sterilize the touch screen at start-up, and periodically during operation.

In a further aspect, the LEDs are disposed at the edges of the glass display such that angles of reflection retain the UV rays within the glass display to prevent damage or strain to the user's eyes.

In a further aspect, the LEDs are disposed behind the glass display, potentially also behind a UV fluorescing or phosphorescing layer to sterilize the glass from behind.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
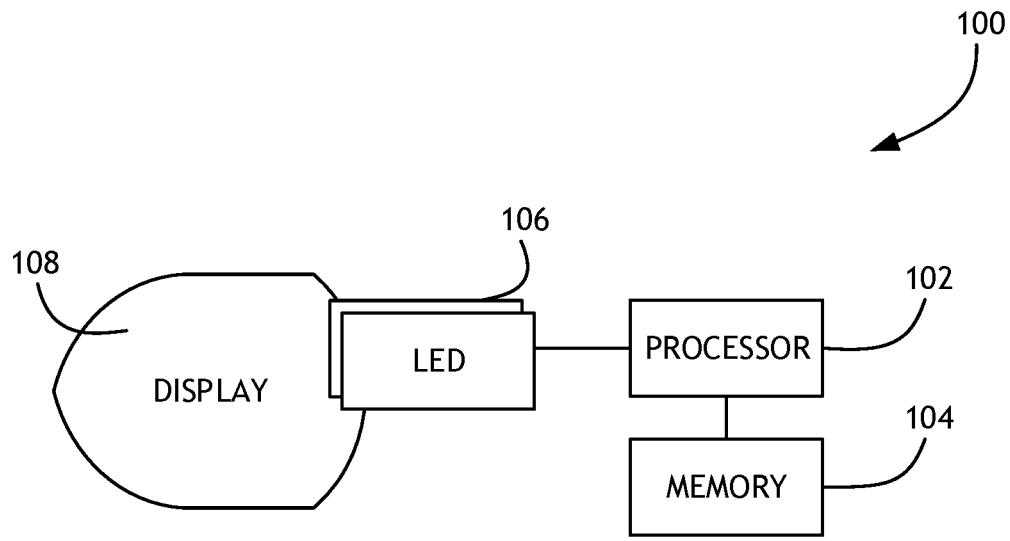
FIG. 1 shows a block diagram of an exemplary embodiment of a computer system according to the inventive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a touch screen with built-in ultraviolet (UV) light-emitting diodes (LEDs). The LEDs sterilize the touch screen at start-up, and periodically during operation.

Referring to FIG. 1, a block diagram of an exemplary embodiment of a computer system 100 according to the inventive concepts disclosed herein is shown. The system 100 includes a processor 102, memory 104 connected to the processor 102, and a plurality of LEDs 106 connected to the processor. The LEDs 106 may be organic light emitting diodes (OLEDs) or MicroLEDs with a UV component. The system 100 may be part of a touch screen display 108 or an external bolt-on appliance for an existing touch screen display 108. The LEDs 106 are organized proximal to the touch screen display 108 so as to illuminate substantially the entire touch surface of the touch screen display 108.

In at least one embodiment, the processor 102 activates the LEDs 106 during a start-up procedure to sterilize the touch screen display 108 initially, then deactivates the LEDs 106 to prevent damage or eye-strain during routine use. In another embodiment, the processor 102 activates the LEDs 106 periodically. In another embodiment, the processor 102 identifies when the touch screen display 108 has not been touched for an extended period and activates the LEDs 106 to sterilize the touch screen display 108 during periods of disuse, but not during periods of heavy use.

Figure 2:
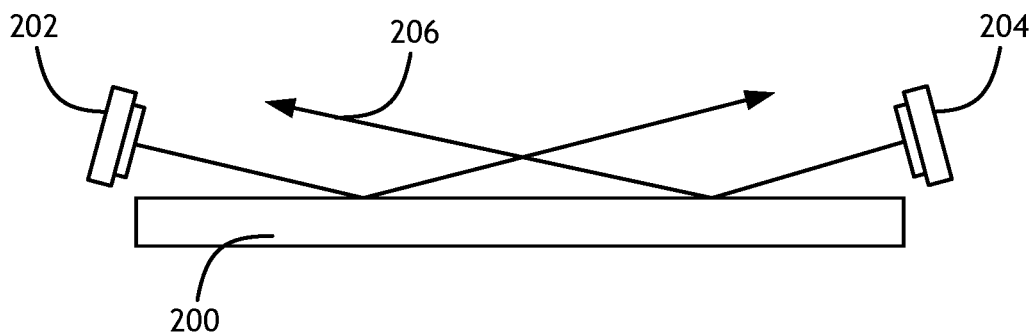
FIG. 2 shows a side view of an exemplary embodiment according to the inventive concepts disclosed herein.

Referring to FIG. 2, a side view of an exemplary embodiment according to the inventive concepts disclosed herein is shown. A touch screen display includes a plurality of LEDs 202, 204 configured to illuminate the front, touch surface of the cover glass 200. In at least one embodiment, the LEDs 202, 204 are disposed at an angle to the cover glass 200 such that the rays 206 emanating from the LEDs 202, 204 and reflecting off the front surface of the cover glass 200 are directed away from a user, or otherwise reduce reflection directly away from the cover glass 200 to prevent eye strain or damage.

In at least one embodiment, the LEDs 202, 204 may be organized into two or more sets of LEDs 202, 204 configured at different angles to illuminate different parts of the cover glass 200. For example, a first set of LEDs 202 may be disposed along a first edge of the cover glass 200 at a first angle and a second set of LEDs 204 may be disposed along a second edge of the cover glass 200 at a second angle; the first angle and second angle having substantially similar magnitude but different direction.

In at least one alternative embodiment, the first set of LEDs 202 may be disposed along an edge at a first angle while a second set of LEDs 204 are disposed along the same edge at a second angle to directly illuminate a different part of the cover glass 200.

Figure 3:
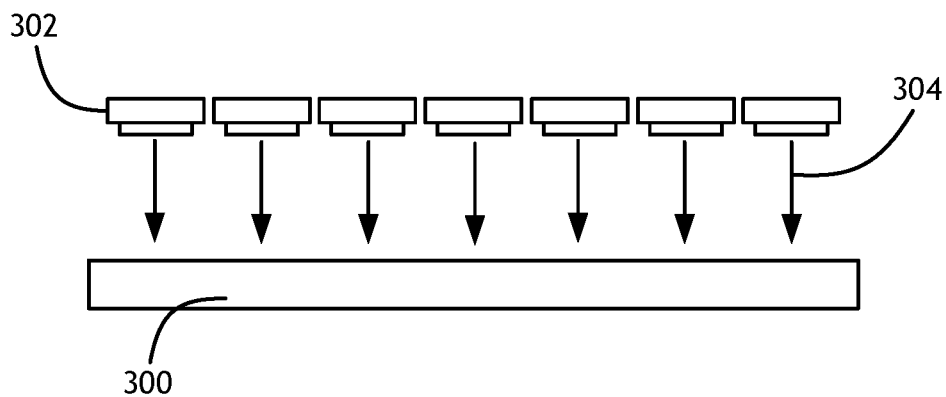
FIG. 3 shows a side view of an exemplary embodiment according to the inventive concepts disclosed herein.

Referring to FIG. 3, a side view of an exemplary embodiment according to the inventive concepts disclosed herein is shown. A touch screen display includes a plurality of LEDs 302 configured to directly illuminate the front, touch surface of the cover glass 300. In at least one embodiment, the LEDs 302 may comprise a transparent or semi-transparent layer such that the rays 304 emanating from the LEDs 302 are substantially orthogonal to the cover glass 300 and may be scattered by the cover glass 300 or by the layer of LEDs 302 upon reflection.

Figure 4:
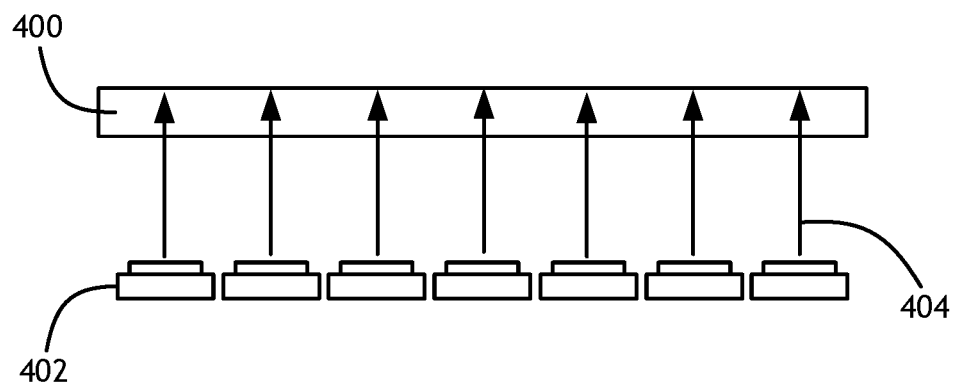
FIG. 4 shows a side view of an exemplary embodiment according to the inventive concepts disclosed herein.

Referring to FIG. 4, a side view of an exemplary embodiment according to the inventive concepts disclosed herein is shown. A touch screen display includes a plurality of LEDs 402 configured to illuminate the cover glass 400 from behind such that the rays 404 emanating from the LEDs 402 pass through the cover glass 400 and are scattered upon passing through the front, touch surface. In at least one embodiment, the LEDs 402 may comprise a transparent or semi-transparent layer. In at least one embodiment, the LEDs 402 may be incorporated into the display array.

Figure 5:
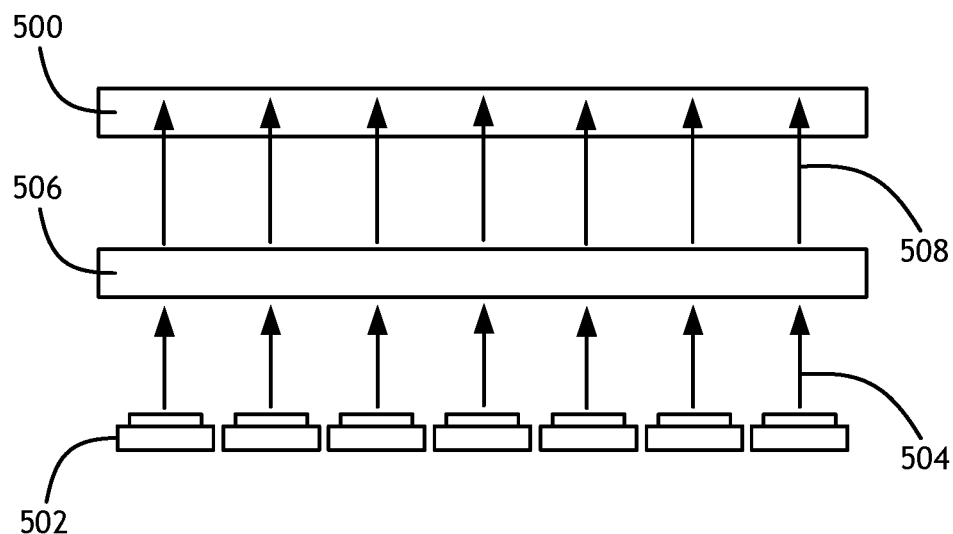
FIG. 5 shows a side view of an exemplary embodiment according to the inventive concepts disclosed herein.

Referring to FIG. 5, a side view of an exemplary embodiment according to the inventive concepts disclosed herein is shown. A touch screen display includes a plurality of LEDs 502 configured to produce rays 504 of a specific frequency to illuminate an intermediate layer 506. The intermediate layer 506 may comprise a UV fluorescing material or phosphorescing material that produces diffuse UV light 508 upon illumination by the rays 504. The diffuse UV light 508 illuminates the cover glass 500 from behind. In at least one embodiment, the LEDs 502 and intermediate layer 506 may comprise transparent or semi-transparent layers. Alternatively, a display layer may be interposed between the cover glass 500 and the LEDs 502, provided the display layer allows transit of UV light to sterilize the front surface of the cover glass 500.

Figure 6:
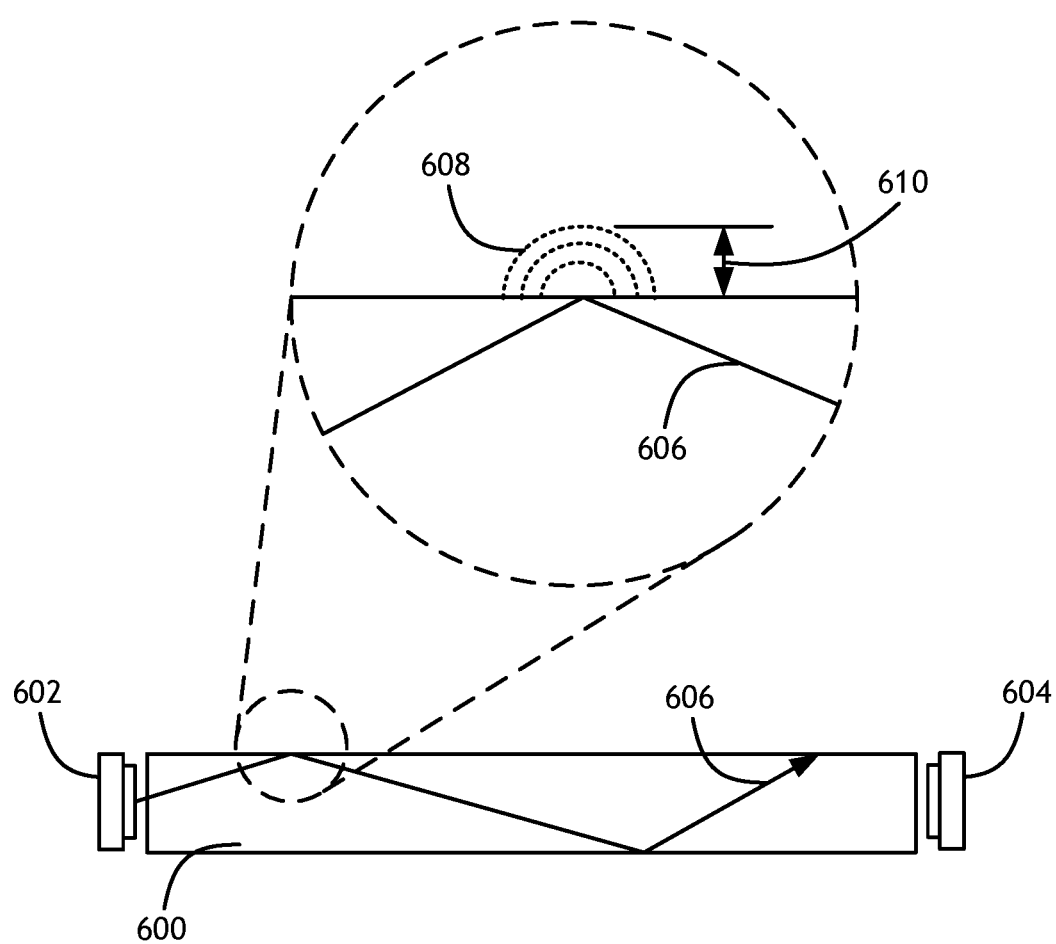
FIG. 6 shows a side view and close-up view of an exemplary embodiment according to the inventive concepts disclosed herein.

Referring to FIG. 6, a side view and close-up view of an exemplary embodiment according to the inventive concepts disclosed herein is shown. A touch screen display includes a plurality of LEDs 602, 604 disposed to directly illuminate the edges of the cover glass 600. The LEDs 602, 604 and cover glass 600 are configured such that the rays 606 emanating from the LEDs 602, 604 experience total internal reflection. At every point where a ray 606 reflects from at least the front surface, a standing evanescent wave 608 is produced having a wavelength 610 corresponding to the ray 606.

In at least one embodiment, the LEDs 602, 604 may be organized into two or more sets of LEDs 602, 604 disposed at different edges of the cover glass 600 with all rays 606 from each of the LEDs 602, 604 configured for total internal reflection.

Figure 7:
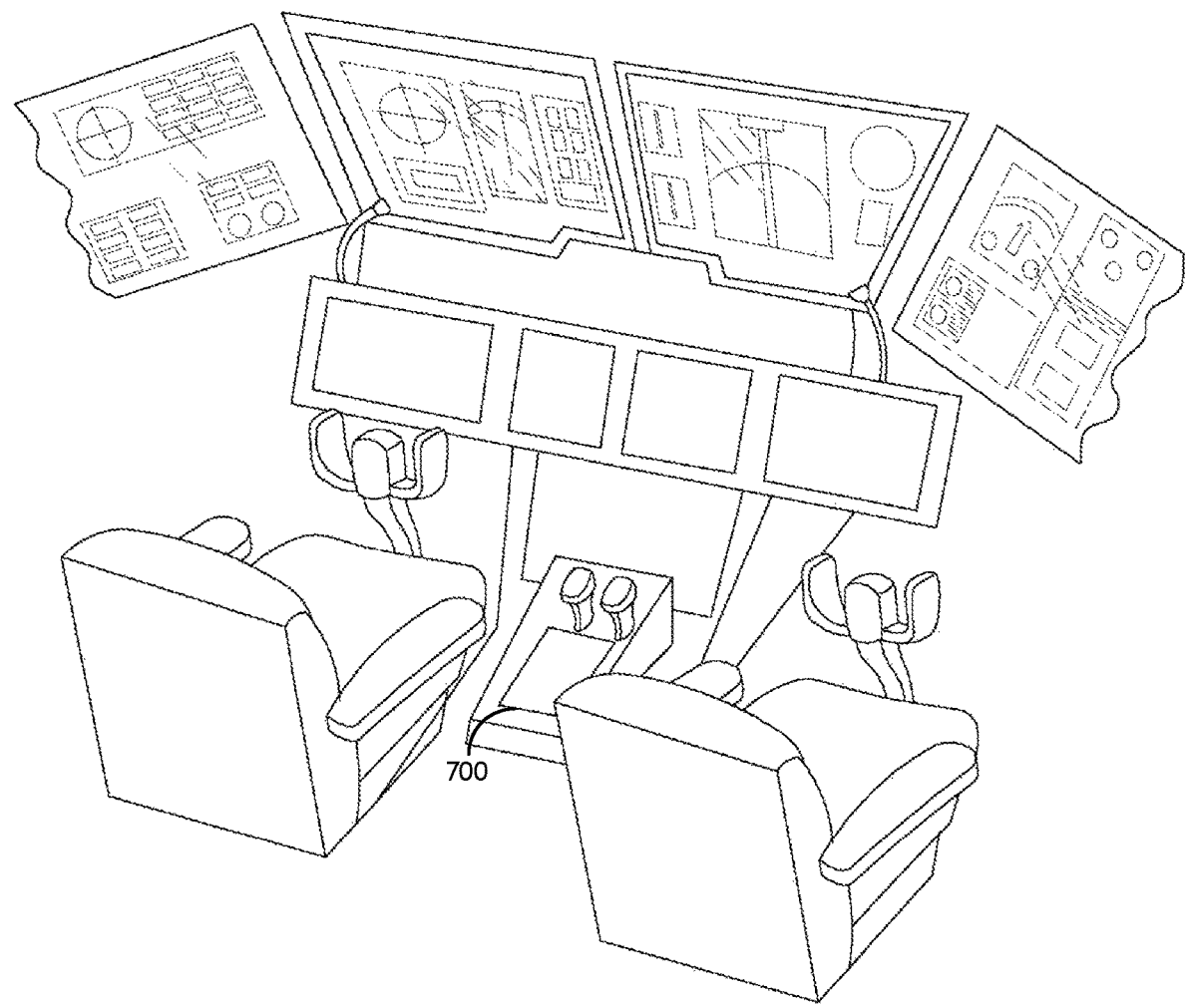
FIG. 7 shows an environmental view of an exemplary embodiment according to the inventive concepts disclosed herein.

Referring to FIG. 7, an environmental view of an exemplary embodiment according to the inventive concepts disclosed herein is shown. Touch screen display devices 700 in an aircraft cockpit may include embodiments of the inventive concepts disclosed herein.

Figure 8:
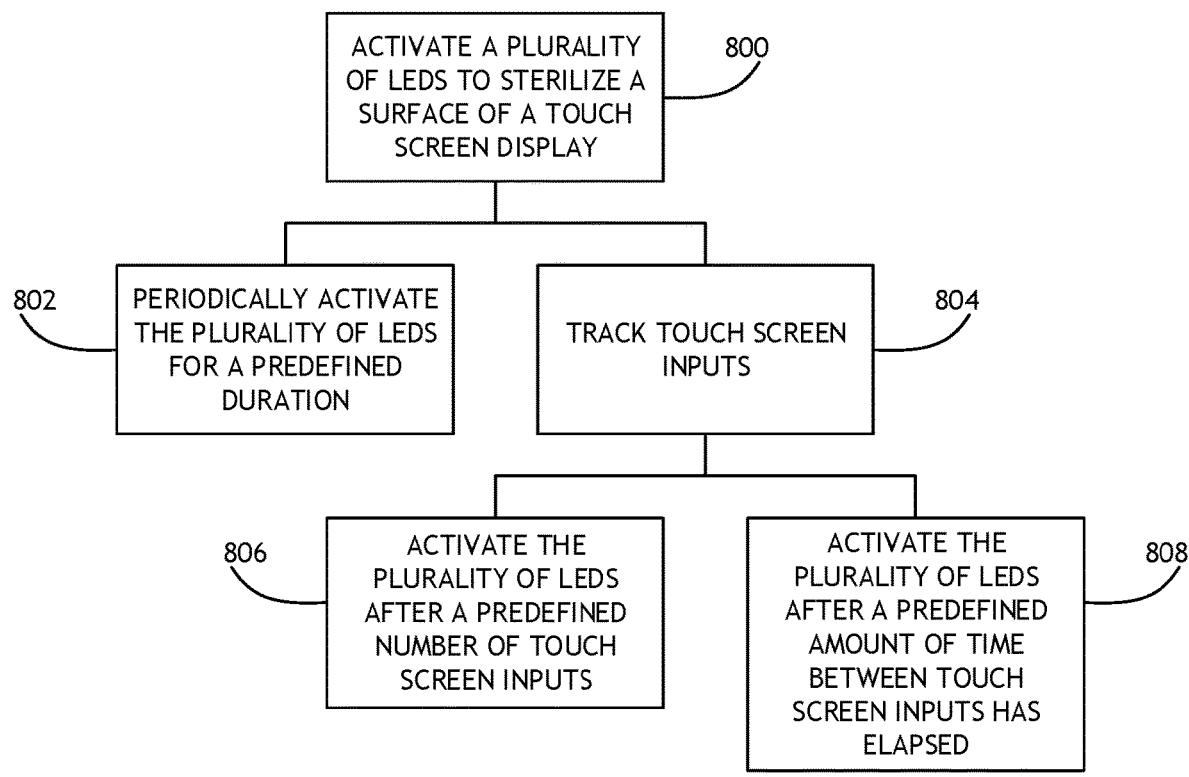
FIG. 8 shows a flowchart of a method according to an exemplary embodiment of the inventive concepts disclosed herein.

Referring to FIG. 8, a flowchart of a method according to an exemplary embodiment of the inventive concepts disclosed herein is shown. During a startup process of a touch screen enabled computer system, a plurality of LEDs are activated 800 to sterilize the touch screen. In at least one embodiment, the LEDs produce a UV light. In one or more alternative embodiments, the LEDs produce a wavelength of light configured to interact with a fluorescing layer or phosphorescing layer to produce UV light.

In at least one embodiment, the LEDs are periodically activated 802 during normal operations, and for a predefined period, to sterilize the touch screen in intervals. Alternatively, or in addition, a system implementing embodiments of the inventive concepts disclosed herein may track 804 touch screen inputs. Where the system tracks 804 touch screen inputs, the plurality of LEDs may be activated 806 after a predefined number of touch screen inputs to sterilize the touch screen of a statistically define germ load such that the power and duration of the UV light required to sterilize the touch screen may be know within a certain range. Alternatively, the plurality of LEDs may be activated 808 after a predefined duration with no touch screen inputs such that the touch screen is sterilized whenever an operation is completed.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
a touch screen display device;
a plurality of light-emitting diodes (LEDs) disposed along at least one edge of the touch screen display device, a first set of the plurality of LEDs disposed at a first angle to and above a first edge, and a second set of the plurality of LEDs disposed at a second angle to and above the first edge;
at least one processor in data communication with the plurality of LEDs and with a memory storing processor executable code for configuring the at least one processor to:
activate the plurality of LEDs for a predetermined period of time to sterilize a touch screen display device with ultraviolet (UV) light during a startup operation; and
periodically activate the plurality of LEDs for the predetermined period of time to sterilize the touch screen display device with UV light during operation.

2. The computer apparatus of claim 1, wherein the plurality of LEDs are disposed around a perimeter of the touch screen display device.

3. The computer apparatus of claim 2, wherein a set of LEDs in the plurality of LEDs are disposed around the perimeter of the touch screen display device such that rays from each the plurality of LEDs are internally reflected within a cover glass of the touch screen display device to produce standing evanescent waves at a front surface.

4. The computer apparatus of claim 1, wherein a set of LEDs in the plurality of LEDs are disposed behind a cover glass of the touch screen display device.

5. The computer apparatus of claim 4, further comprising a fluorescing layer disposed between the set of LEDs and the touch screen display device, wherein the plurality of LEDs are configured to induce UV fluorescence in the fluorescing layer.

6. The computer apparatus of claim 1, further comprising a plurality of UV LED elements of a display array of the touch screen display device.

7. A method comprising:
activating a plurality of LEDs for a predetermined period of time to sterilize a touch screen display device with ultraviolet (UV) light during a startup operation; and
periodically activating the plurality of LEDs for the predetermined period of time to sterilize the touch screen display device with UV light during operation,
wherein the plurality of LEDs are disposed along at least one edge of the touch screen display device, a first set of the plurality of LEDs disposed at a first angle to and above a first edge, and a second set of the plurality of LEDs disposed at a second angle to and above the first edge.

8. The method of claim 7, further comprising tracking touch screen display device inputs.

9. The method of claim 8, wherein periodically activating the plurality of LEDs comprises activating the plurality of LEDs after a predetermined number of touch screen display device inputs.

10. The method of claim 8, wherein periodically activating the plurality of LEDs comprises activating the plurality of LEDs after a predetermined duration without any touch screen display device inputs.

11. The method of claim 7, further comprising fluorescing UV light from a fluorescing layer based on light received from the plurality of LEDs.

12. The method of claim 7, further comprising internally reflecting the UV light within a cover glass of the touch screen display device to produce a standing evanescent wave.

13. A aircraft comprising:
a cockpit touch screen display device;
a plurality of light-emitting diodes (LEDs) disposed along at least one edge of the touch screen display device, a first set of the plurality of LEDs disposed at a first angle to and above a first edge, and a second set of the plurality of LEDs disposed at a second angle to and above the first edge;
at least one processor in data communication with the plurality of LEDs, the cockpit touch screen display device, and with a memory storing processor executable code for configuring the at least one processor to:
activate the plurality of LEDs for a predetermined period of time to sterilize the cockpit touch screen display device with ultraviolet (UV) light during a startup operation; and
periodically activate the plurality of LEDs for the predetermined period of time to sterilize the cockpit touch screen display device with UV light during operation.

14. The aircraft of claim 13, wherein a set of the plurality of LEDs are disposed around a perimeter of the cockpit touch screen display device.

15. The aircraft of claim 14, wherein a set of the plurality of LEDs are disposed around the perimeter of the cockpit touch screen display device such that rays from each the plurality of LEDs are internally reflected within a cover glass of the cockpit touch screen display device to produce standing evanescent waves at a front surface.

16. The aircraft of claim 13, wherein a set of the plurality of LEDs are disposed behind a cover glass of the cockpit touch screen display device.

17. The aircraft of claim 16, further comprising a fluorescing layer disposed between the set of LEDs and the cockpit touch screen display device, wherein the set of LEDs are configured to induce UV fluorescence in the fluorescing layer.

18. The aircraft of claim 13, further comprising a plurality of UV LEDs elements of a display array of the cockpit touch screen display device.

* * * * *